United States Patent [19]

Seely et al.

[11] 3,994,972

[45] Nov. 30, 1976

[54] SYNTHESIS OF N,N',N'',N'''-TETRA-SALICYLIDENE PENTAERYTHRITYL TETRAMINE

[75] Inventors: Michael J. Seely, Chagrin Falls; Thomas C. Peterson, Cuyahoga Falls, both of Ohio

[73] Assignee: Horizons Incorporated, a division of Horizons Research Incorporated, Cleveland, Ohio

[22] Filed: June 30, 1975

[21] Appl. No.: 591,872

[52] U.S. Cl. .................... 260/556 S; 260/239 A; 260/566 F; 260/583 P
[51] Int. Cl.² .................................. C07C 143/78

[58] Field of Search ......... 260/566 R, 566 F, 583 P, 260/239 A, 556 S

[56] References Cited
OTHER PUBLICATIONS

Organic Synthesis Collected, vol. 4, pp. 753–755.
J.C.S. pp. 1588–1595 (1938).

*Primary Examiner*—Gerald A. Schwartz
*Attorney, Agent, or Firm*—Lawrence I. Field

[57] ABSTRACT

An improved synthesis of N,N',N'',N'''-tetra-salicylidene pentaerythrityl tetramine via pentaerythrityl benzene or toluene sulfonates.

10 Claims, No Drawings

SYNTHESIS OF N,N',N'',N'''-TETRA-SALICYLIDENE PENTAERYTHRITYL TETRAMINE

This invention relates to an improved synthesis of N,N',N'',N'''-tetra-salicylidene pentaerythrityl tetramine, a compound which has been described as a useful additive to hydraulic fluids (see U.S. Pat. No. 3,468,802 issued Sept. 23, 1969 to Donald H. Nail) and which is also known to be useful as a chelating agent.

A number of methods of synthesizing pentaerythrityl tetramine have been reported in the literature including the following:

1. Preparation from pentaerythrityl bromide, as reported by Litherland and Mann in Journal Chemical Society (1938) pp. 1588–1595;
2. Preparations involving reduction of the tetrazide as described by Fleischer, Gebalay, Lavey, and Tasker, Journal of Organic Chemistry (1971) 36 3042–3044.

The preparation of N,N',N'',N'''-tetra-salicylidene pentaerythrityl tetramine is described in the following:

R. W. Oehmke and J. C. Bailor, Jr., J. Inorg. Nuclear Chem. (1965), 27, 2199–2207

A. J. Chalk and J. F. Smith, Transactions of the Faraday Soc., 53, 1235–1245 (1957)

Both of these articles cite Litherland and Mann, J.C.S. (1938), 1588–1595 as the source for pentaerythrityl tetramine.

The present invention is directed to improvements in these and other previously known methods of synthesis of N,N',N'',N'''-tetra-salicylidene pentaerythrityl tetramine.

Specifically, in the present invention (1) pentaerythritol is converted to the tetratosylamide through the benzenesulfonate derivative rather than the tetrabromide used by Litherland and Mann, and (2) a means is provided for preparing and converting an azetidine into tetratosylamide whereby the overall yield in the process is improved.

Further, the present invention avoids the tetrazide, which is a very shock sensitive material and therefore presents an explosion risk.

Briefly, the process of the present invention comprises the following sequence of steps:

1. reaction of pentaerythritol by known procedures to produce pentaerythrityl tetrabenzenesulfonate (I), pentaerythrityl tetratoluene-sulfonate or other esters of similar nature;
2. reaction of (I) with either 8 molar equivalents of NaNHTs in an aprotic solvent to give $C(CH_2NHYs)_4$ directly or with 6 molar equivalents of NaNHTs in an aprotic solvent to give

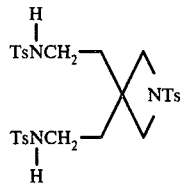
(II)

and then reaction of (II) with another equivalent of NaNHTs either in an aprotic solvent or liquid melt to yield $C(CH_2NHTs)_4$ indirectly;

3. hydrolysis of $C(CH_2NHTs)_4$ to yield $C(CH_2NH_2)_4$ and then;
4. condensation of the tetramine with salicylaldehyde by known procedures.

As described in the literature, tetrakis-(p-toluene sulfonamidomethyl) methane can be prepared by the following reaction:

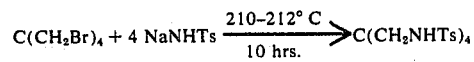

Besides being low yield, this reaction must be done on a very small scale in order to insure uniform heating of the mixture which even at the indicated temperature does not become a fluid stirrable melt.

Liquid chromatographic analysis showed that this reaction proceeds through two heterocyclic intermediates. Utilizing a polar aprotic solvent and increasingly vigorous conditions, the reaction can be caused to proceed in stages through these intermediates:

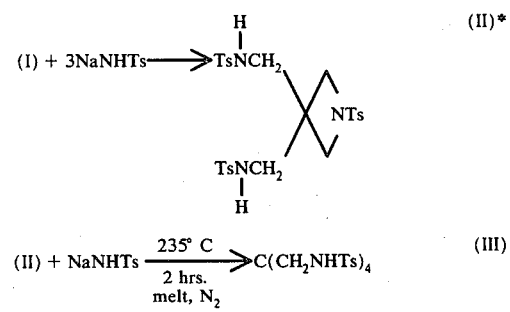

*This reaction itself may proceed in two stages as

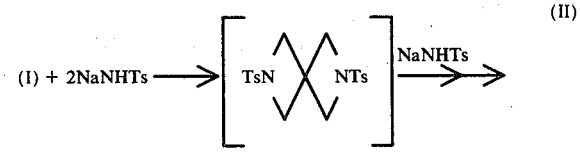

By the use of the polar aprotic solvent, the azetidine (II) is obtained in good yield. In order to convert (II) to the desired product, the final substitution can be effected in a fused melt at temperatures in the range of 220°–250° C, 235° C being a preferred temperature, or it can be accomplished at 190°–225° C in hexamethylphosphoramide (HMPA).

In the sequence depicted above, it was found that each successive substitution requires more time and increasingly vigorous reaction conditions. In addition, it was found that the azetidine (II) is prepared in good yield by reacting pentaerythrityl tetrabenzenesulfonate with excess sodium p-toluenesulfonamide in dimethyl sulfoxide (DMSO). This azetidine can be converted to the desired tetrasulfonamide in a final high temperature step. It was further found that the use of HMPA as the reaction medium allows the direct preparation of the tetrasulfonamide from pentaerythrityl tetrabenzenesulfonate in high yield.

The reaction sequences of this invention may be depicted as follows:

1. Preparation of pentaerythrityl tetrabenzenesulfonate by the technique described in Organic Synthesis Collected Vol. 4, pages 753–755

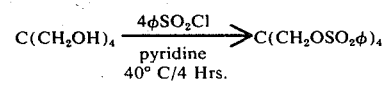

2. Direct route for preparation of the tetrasulfonamide:

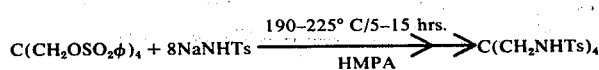

or indirect route for preparation of the tetrasulfonamide:

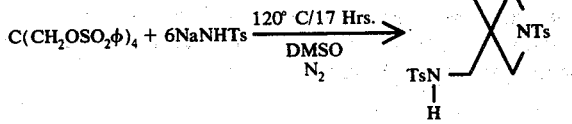

followed by

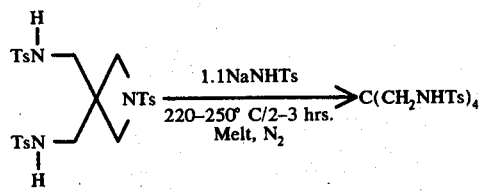

or

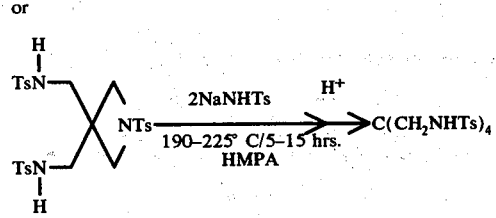

3. Thereafter the products are reacted by known procedures as described in J.C.S. (1938) 1588–95 as follows:

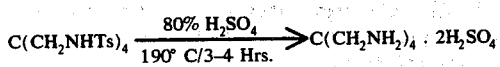

and then

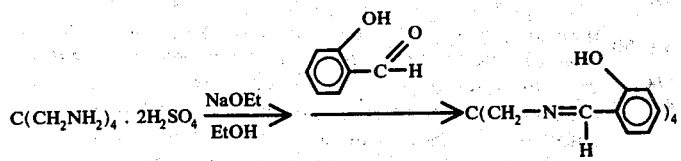

The invention will be further understood from the description which follows illustrating the several steps in the above sequence.

Pentaerythrityl tetra(benzenesulfonate) was prepared by any known method, for example, by the method described in Organic Synthesis Collected Volume 4 pages 753–755 and the product was purified by recrystallization from methanolethyl acetate (3v/1v) mixture.

Sodium p-toluene sulfonamide was also prepared by known methods, for example, by the method described in The Journal of the Chemical Society (1938) pages 1588–1595.

The two were reacted to produce tetrakis-(p-toluenesulfonamidomethyl)-methane, directly or indirectly in accordance with the following examples.

Direct Route

Tetrakis-(p-toluenesulfonamidomethyl)-methane 15.4 g sodium p-toluenesulfonamide ($8 \times 10^{-1}$m) and 100 ml hexamethylphosphoramide (HMPA) are combined and heated to 220, $\pm 5°$ C with stirring under nitrogen. 7.0 g pentaerythrityltetrabenzenesulfonate ($1 \times 10^{-2}$m) are then added over five minutes and the light yellow solution maintained at the above temperature range for 5 hours under a blanket of nitrogen.

On cooling the reaction mixture forms a suspension. This suspension is poured into 1 liter of water with stirring and the resultant milky mixture heated to 45° C. The precipitated sulfonamides are filtered and the filtrate saved for later HMPA recovery. The filter cake is washed with water until the filtrates are neutral and then dried at 40° C under vacuum. (A methanol wash can be used following the water washes to speed drying.) After drying there remains 6.8 g crude tetrasulfonamide. The crude product is purified by boiling several minutes with 35 ml 3:1 (w/w) acetic acid-water. The fine white suspension is filtered while hot and the filter cake washed with dilute acetic acid followed by water until the filtrates are neutral. After drying under vacuum at 40° C, 6.1 g purified tetrasulfonamide are obtained (81.4% theory) m.p. 250°–252° C. HMPA is recovered as follows: The filtrate from the sulfonamide precipitation is extracted with 2 ×500 ml chloroform. The pooled chloroform extracts are dried ($K_2CO_3$) and evaporated at 30° C under reduced pressure to leave 200 ml of a HMPA-chloroform complex. The evaporator's bath temperature is raised to 80° C thereby destroying the complex and distilling out the balance of the chloroform. 750 ml chloroform and 107 ml light yellow crude HMPA are obtained. Finally, the crude HMPA is vacuum distilled at 86°–88° C/2 mm to give 72 ml pure HMPA. The overall recovery is 75% for chloroform and 72% for HMPA.

Indirect Route

Preparation of
3,3-Bis-(p-Toluenesulfonamidomethyl)-N-(p-Tosyl)-Azetidine 1664 g Sodium p-toluenesulfonamide (8.6 moles), 2727 ml DMSO (3 kg, Aldrich 99% +) and 1000 g pentaerythrityl tetrabenzenesulfonate (1.4 moles) are combined in a 12 liter four-necked round bottomed flask fitted with mantle, mechanical stirrer, thermometer, and nitrogen inlet-outlet. The mixture is stirred and heated at 118°–120° C for 17 hours under a blanket of nitrogen and then allowed to cool. The light yellow slurry is then poured with rapid stirring into a mixture of ice and water. The white to light yellow suspension is stirred well to break up any large chunks of precipitate and then the solid collected on several large fritted funnels. The solid is washed well with water until the filtrates are nearly neutral. Then the crude azetidine is washed with methanol and pressed dry. After drying in a vacuum oven at 60° C, approximately 777 g crude azetidine are obtained. The impurities are removed by recrystallizing the crude product from 3:1 (w/w) acetic acid-water using approximately 867 ml solvent per 100 g azetidine. From the recrystallization 601 g pure 3,3-bis-(ptoluenesulfonamidomethyl)-N-(p-tosyl)-azetidine are obtained, 72% theory (the melting point of the recrystallized azetidine is 210°–212° C).

Preparation of
Tetrakis-(p-Toluenesulfonamidomethyl)-Methane 450 g 3,3-bis(p-toluenesulfonamidomethyl)-N-(p-tosyl)-azetidine (7.8 × 10⁻¹ moles) are melted in a one liter three necked round bottomed flask partially immersed in an oil bath at 237° C. The flask is fitted with nitrogen inlet-outlet, mechanical stirrer (glass paddle) and thermometer. Addition of the azetidine requires about 1.5 hours. Any DMSO vapors given off during the melting should be urged from the system with nitrogen. 158 g Sodium p-toluenesulfonamide (8.2 × 10⁻¹ mole or 5% excess) are then added with stirring at a rate which maintains fluidity of the reaction mixture. Shortly after completing the addition the reaction mixture will become a clear amber solution. At this point, the stirrer is stopped and the solution allowed to heat at 235° C for an additional 1-¼ hours. The total heating time since the beginning of the addition should not exceed 2.5 hours. Otherwise, excessive charring may be encountered. Then the melt is poured onto a sheet of aluminum foil and allowed to cool. The crude tetrasulfonamide weighs about 606 g.

The brittle, amber solid is powdered and then extracted by boiling, with rapid stirring, two minutes with 2425 ml 3:1 (w/w) acetic acid-water. The suspension is filtered hot to obtain tetrasulfonamide of about 90% purity. After washing with fresh dilute acetic acid and then water; the filter cake is dried in a vacuum oven to yield about 410 g purified tetrasulfonamide. Yields range from 71 to 77% theory. The melting point of the pure tetrasulfonamide is 248°–250° C (JCS (1938), 1588–1595).

We claim:
1. In a process for the preparation of pentaerythrityl tetra-tosylamide in which pentaerythritol is converted to a pentaerythrityl tetraarylsulfonate and then said tetraarylsulfonate is reacted with an alkali toluenesulfonamide to produce a pentaerythrityl tetra-tosylamide, also known as tetrakis-(p-toluenesulfonamidomethyl)-methane, the improvement which consists in carrying out said reaction in an aprotic solvent.

2. The process of claim 1 wherein said tetraarylsulfonate is selected from the group consisting of tetrabenzene sulfonate and tetratoluene sulfonate.

3. The process of claim 1 wherein each mol of the tetraarylsulfonate is reacted with about 8 molar equivalents of sodium tosylamide to yield pentaerythrityl tetrasulfonamide.

4. The process of claim 3 wherein the aprotic solvent is HMPA.

5. The process of claim 4 wherein the reaction is conducted at a temperature of 190°–225° C for 5 to 15 hours.

6. The process of claim 1 wherein each mol of said tetraarylsulfonate is reacted first with about 6 molar equivalents of sodium p-toluenesulfonamide to produce as an intermediate 3,3-bis-(p-toluenesulfonamidomethyl)-N-(p-toyl)-azetidine and subsequently with up to two additional molar equivalents of sodium p-toluenesulfonamide, to produce tetrakis-(p-toluenesulfonamidomethyl)-methane.

7. The process of claim 6 wherein the first reaction is conducted in DMSO or diethylene glycol at 110°–175° C for 5–20 hours.

8. The process of claim 6 wherein in the subsequent reaction the 3,3-bis-(p-toluenesulfonamidomethyl)-N-(p-tosyl)-azetidine is reacted in a melt at 220°–250° C for 2–3 hours.

9. The process of claim 6 wherein in the subsequent reaction the 3,3-bis-(p-toluenesulfonamidomethyl)-N-(p-tosyl)-azetidine is reacted in HMPA at 190°–225° C for 5 to 15 hours.

10. The process of claim 1 wherein the pentaerythrityl tosylamide is hydrolyzed to pentaerythritol tetraamine which is then converted to N,N',N'',N'''-tetrasalicylidne pentaerythrityl tetraamine.

* * * * *